(12) United States Patent
Liotta

(10) Patent No.: US 6,945,998 B2
(45) Date of Patent: Sep. 20, 2005

(54) CORPORAL IMPLANTATION DEVICE FOR ASSISTING BLOOD AND HEART VENTRICULAR CIRCULATION

(76) Inventor: Domingo Santo Liotta, 3 de Febrero 2025, 8$^{th}$ Floor, (1428) Buenos Aires (AR)

( * ) Notice: Subject to any disclaimer, the term of this patent is extended or adjusted under 35 U.S.C. 154(b) by 50 days.

(21) Appl. No.: 10/319,244

(22) Filed: Dec. 13, 2002

(65) Prior Publication Data

US 2004/0054251 A1 Mar. 18, 2004

(30) Foreign Application Priority Data

Sep. 18, 2002 (AR) ........................................ P020103517

(51) Int. Cl.$^7$ .............................................. A61M 1/12
(52) U.S. Cl. ........................ 623/3.2; 623/3.21; 600/16
(58) Field of Search .............................. 623/FOR 102, 623/3.1–3.12, 3.16–3.27; 600/16

(56) References Cited

U.S. PATENT DOCUMENTS 5,006,104 A * 4/1991 Smith et al. .................. 600/16
5,397,349 A * 3/1995 Kolff et al. .................. 623/3.3

OTHER PUBLICATIONS

Liotta, An article entitled, "Novel Left Ventricular Assist System", By Liotta, published 2003 by the Texas Heart Institute Journal, pp. 194–201; vol. 30, Nov. 3, 2003.

Liotta, An article entitled "Novel Left Ventricular Assist System II", By Liotta, published 2004 by the Texas Heart Institute Journal, pp. 278–282; vol. 31, Nov. 3, 2004.

* cited by examiner

Primary Examiner—David H. Willse
(74) Attorney, Agent, or Firm—Bachman & LaPointe, P.C.

(57) ABSTRACT

A dual pusher-plate blood pump implanted into the body with either mechanical or biological valves (17) for unidirectional blood circulation through a circulation variable chamber (blood chamber) (12) to assist circulation. LVAS comprises a receptacle (housing) (4) provided with an inlet (3) and an outlet (5) The pump inflow (3) is connected to the left atrium and the pump outflow to the descending thoracic aorta (5,7) and a pulsating external pneumatic unit (8).

35 Claims, 8 Drawing Sheets

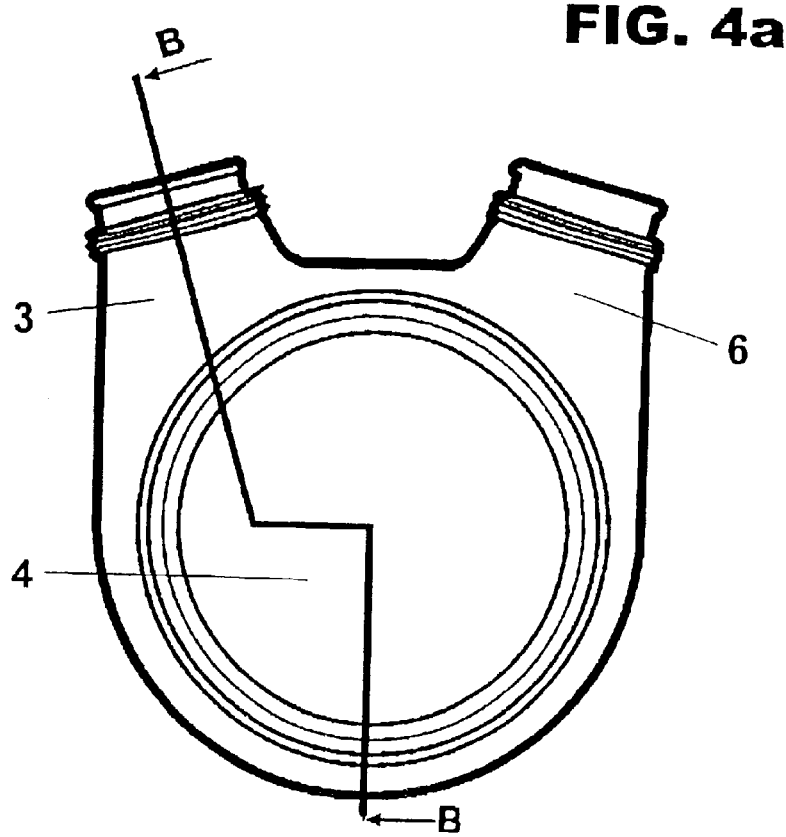
FIG. 4a
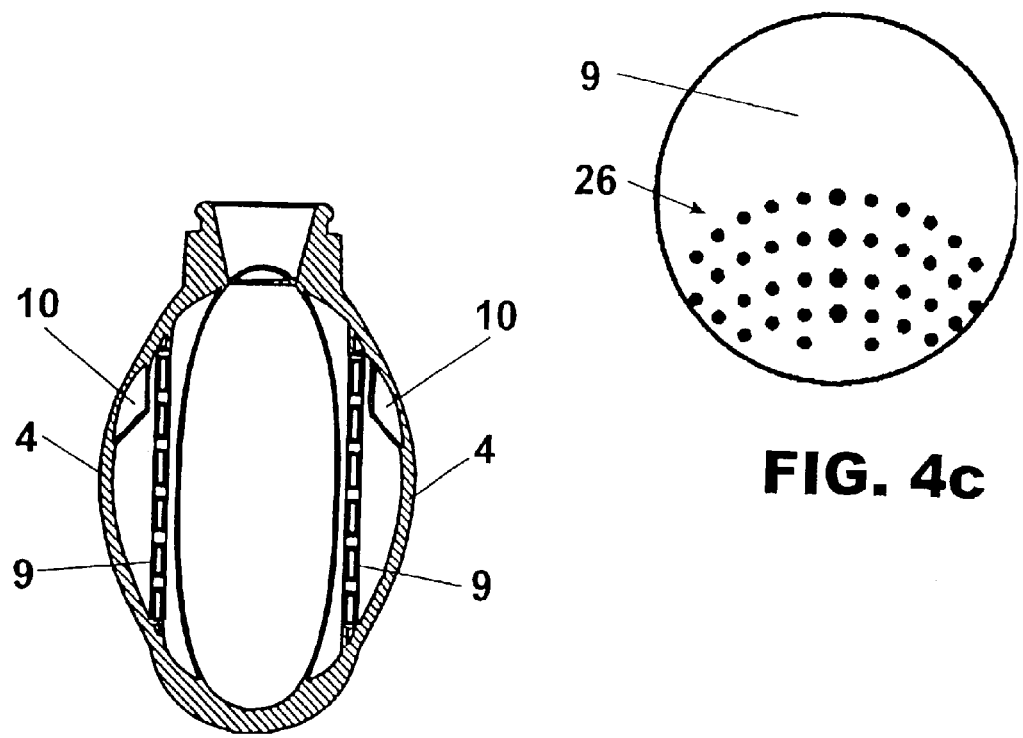
FIG. 4c
FIG. 4b

FIG. 5a
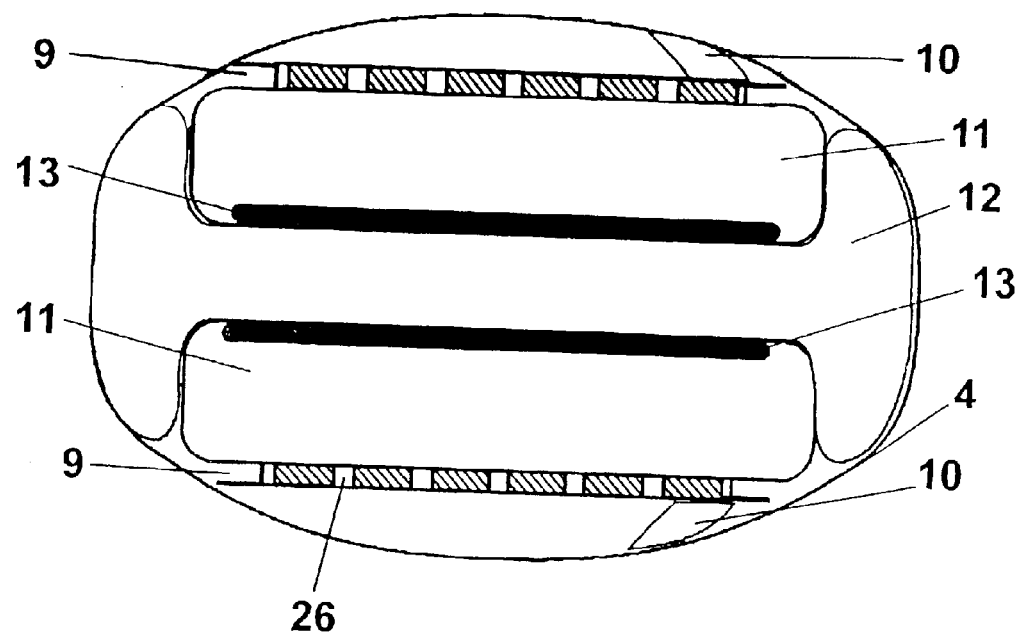
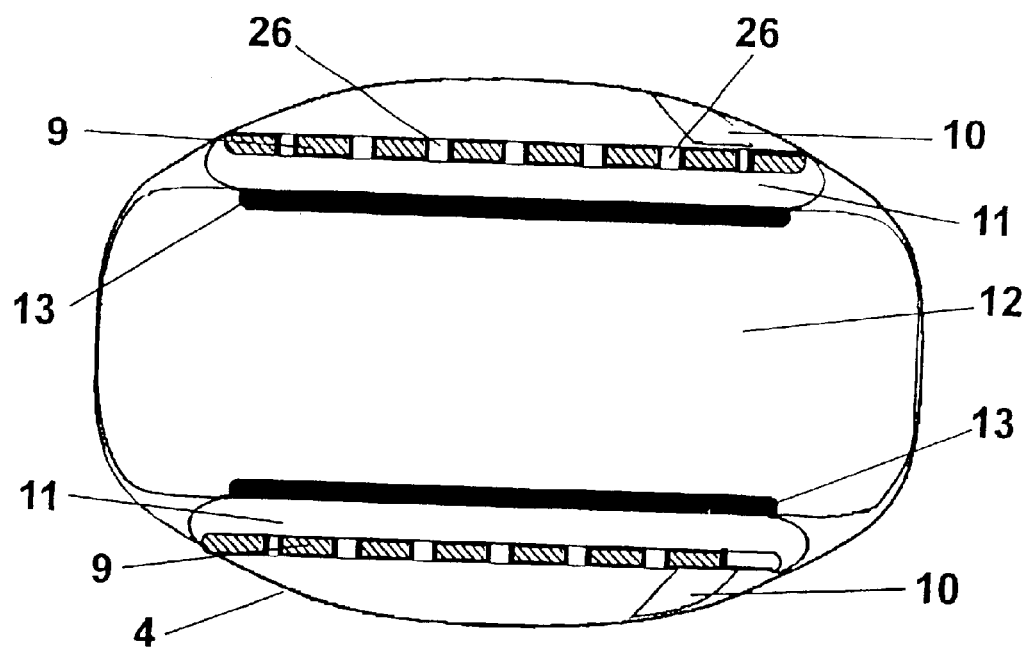
FIG. 5b

CORPORAL IMPLANTATION DEVICE FOR ASSISTING BLOOD AND HEART VENTRICULAR CIRCULATION

FIELD OF THE INVENTION

The instant invention relates to a Corporal Implantation Device for Assisting heart Blood and Ventricular Circulation; and constitutes a further development—including substantial improvements—on Argentine patent No. 254,898 and U.S. Pat. No. 5,456,715 directed to a system for treating patients with advanced heart insufficiency, whether acute or chronic, refractory to any medical-pharmacological or surgical heart treatment.

Consequently, the Background of the Invention and Prior Art of U.S. Pat. No. 5,456,715 also applies to this application, with the addition of the enormous advance in this medical field during last years.

In fact, work on Mechanical circulatory Assistance began in Houston, Tex., in the sixties [1–8]

HISTORY OF ASSISTED CIRCULATION

1) Liotta D., Taliani T., Giffoniello A. H., Sarria Deheza F., Liotta S., Lizarraga R., Tolocka R., Pagano J., Biancciotti E.: Artificial Heart in the chest: Preliminary report. Trans. Amer. Soc. Int. organs, 1961, 7:318–322.

2) Liotta D., Taliani T., Giffoniello A. H., Lizarraga R., Tolocka R., Pagano J.: Ablation expérimentale et replacement du coeur par un coeur artificiel intrathoracique. Lyon Chirurgical, 1961, 57:704.

3) Liotta D., Crawford E. S., Cooley D. A., De Bakey M. E., Urquia M., Feldman L.: Prolonged partial left ventricular bypass by means of an intrathoracic pump implanted in the left chest. Trans. Amer. Soc. Artif. Int. organs., 1962, 8:90–99.

4) Liotta D., Hall C. W., Henly W. S., Beall A. C., Cooley D. A., De Bakey M. E.: Prolonged Assisted circulation after cardiac or aortic surgery. Prolonged partial left ventricular bypass by means of intracorporeal circulation. This paper was finalist in: The Young Investigators Award Contest of the American College of Cardiology. Denver, Mayo 1962. Amer. J. Cardiol 1963, 12:399–405.

5) DeBakey M. E., Liotta D, Hall C W. Left-heart bypass using an implantable blood pump. Mechanical devices to assist the failing heart. Washington, D.C.: National academy of Sciences-National Research Council, 1966:223–39.

6) DeBakey M. E., Left ventricular bypass pump for cardiac assistance. Clinical experience. Am. J. Cardiol. 1971, 12:3–11.

7) Liotta D., Hall C. W., Villanueva A., O'Neal R. M., De Bakey M. E., A pseudoendocardium for implantable blood pump. Trans.Amer.Soc. Artif. Int. Organs. 1966, 12:129–134.

8) Liotta D., Early clinical application of Assisted Circulation. Texas Heart Institute Journal. 2002; 29: 229–230.

FIG. 1 (Prior Art) is a drawing of the clinical prototype developed by Domingo Liotta Jul. 19, 1963. This prototype was made at Baylor University, Houston; the pump is shown in the diastolic period. The original clinical prototype (Jul. 19, 1963) is shown at the Smithsonian Institution, Washington, D.C.

References of the drawing were as follows: 1-Left Atrium (LA); 2-Inlet Valve; 3-Pump Housing of Silastic reinforced with Dacron Fabric; 4-Air Chamber; 5-Blood Chamber; 6-Outlet Valve; 7 Descending Thoracic Aorta; 8-Air Supplyplastic tube 4 mm ID".

On Jul. 19, 1963 an assisted circulation intrathoracic pump was implanted in a human being for the first time in the history of medicine by the applicant and Dr. E. Stanley Crawford, at Houston, Tex. The insertion was done into a patient under postcardiotomy cardiogenic shock after aortic valve replacement. The actual clinical prototype of this pump, implanted on Jul. 19, 1963 is at the Smithsonian Institution, Washington D.C., USA. In 1964 Dr Domingo Liotta initiated, with Dr. Michael E. DeBakey, at Houston, Tex., the first implantations in patients of assisted circulation with the pump in a paracorporeal position.

Today, after almost 40 years, the two basic fields in clinical application of assisted circulation have been clearly limited:

1. Left Ventricular Assist System (LVAS) bridge to heart transplantation.
2. Left Ventricular Assist System (LVAS) bridge to Myocardial Recovery.

The instant invention proposes:

1) To serve as effective support and afford high safety to the system using as power source for an intracorporeal blood pump the Patient's linear contraction of both the Latissimus dorsi and the Teres major skeletal muscles, main object of Argentine patent No. 254,898 and U.S. Pat. No. 5,456,715. In fact, in patients highly weakened due to their advanced cardiac disease, it is necessary to couple a system to the muscle power utilization for a variable period of time, a system with an external source of power for maintaining the patient alive until the contraction of skeletal muscles may progressively command the situation.

In this original circulatory assistance strategy 2 stages are foreseen: a—External power source (driver) with pneumatic energy for maintaining the patient alive until the muscle may be conditioned to the second stage: b—patient's autologous energy for linear contraction of the skeletal muscles; the blood pump system has a set of two compressing plates (pusher plates), (disclosed in the mentioned Argentine and U.S. patents) attached to the pneumatic chamber, such plates when driven by the muscle contraction, afford the predetermined systolic movement to the blood chamber; thus the blood pumping system is formed by the pneumatic power at a first stage which may take an undetermined period of time until lineal contraction of the patient's skeletal muscle may progressively act at stage two.

2—The pneumatic system of the instant application, which constitutes an improvement over the mentioned patents,it is basically different from that of the prior art in that the implantation of the pneumatic system is carried out independently from the use of muscle power or energy. I.e., the invention relates to a completely independent system which may be used according to the two basic concepts of modern heart circulatory assistance; namely:

a—to maintain the patient alive while searching a donor for the definite heart transplantation procedure, and b—to serve to recover the native heart (myocardial recovery) assisting the patient's heart for an extended period of time.

The pneumatic system proposed is highly safe for the patient and design and operation are simple.

The implantable device for mechanical circulation of blood and assistance to heart ventricles uses a blood circulation pump, and is characterized in that, being driven by the pneumatic source of power produced by an external system (driver), it may maintain the unidirectional mechanical circulation of blood by means of the introduction of two valves into the pump system and in that the assembly develops parameters which may be homologized with relation to normal circulation in what concerns to blood flow and pressure in the patient's circulatory system and for an extended period of time. The instant invention also claims the use of biological valves (bio-prostheses) in which a shock absorber is introduced at the base of the valve support (seat) in order to decrease, mainly at the valve closure cycle, the intense stress of valve cusps occurring when biological valves are mounted to inextensible tubes; comprising the insertion of the pump into the circulatory circuit, with a novel technique claimed herein, which is of main importance since it is carried out with the patient's heart beating, i.e. without the use of extra corporeal circulation (patient off-pump). Another main feature of the invention is that no cannulae are used inside the heart chambers, but the blood intake to the pump is made directly from an opening in the wall of the left atrium (atriostomy).

Atriostomy technique complies, consequently, with two basic principles:

a—The insertion of the blood circulation mechanical system without subjecting the patient to extracorporeal circulation ("off-pump") and, b—absolute deletion of cannulae into heart chambers (avoiding thromboembolic complications), these principles being claimed herein and, further a third novel principle, c—which is synchronization of the patient's native electrocardiogram (ECG) with the pneumatic power system in order to provide ejection of the artificial pump during the diastolic period of the patient's heart (counter pulsation effect). It is known that severe heart failure in near 80% of patients is caused by arterial coronary insufficiency (ischemic myocardiopathy), main cause of severe circulatory insufficiency; and furthermore, about 70% of normal coronary circulation is effected during the diastolic period of the patient's heart cycle, i.e. when the heart is relaxed; consequently sustained and permanent injection of a new blood wave during diastole to the native heart (counter pulsation), improves irrigation in the patient's cardiac muscle, this principle being basic in the method of recovering the patient's cardiac muscle (myocardial recovery).

BRIEF DESCRIPTION OF THE DRAWINGS

FIGS. 4a and 4b show details through a vertical section of the pump (line B—B), with the 2 pneumatic chambers deleted (as an alternative); in this case systolic pressure of injected gas is contained by the pump body (housing) and acts directly at both sides on the walls of the blood chamber; also, FIG. 4c shows the importance of hole distribution at the apex of the diffuser or screen of injected gas in this model in which pneumatic chambers are deleted.

FIGS. 5a and 5b are schemes of the pump unit when the two pneumatic chambers are used. FIG. 5a shows the pump in systole and FIG. 5b the pump in diastole.

FIG. 7a: Atrial prosthesis is sutured to the left atrial wall at its base (outer atrial area). In this scheme, monofilament thread continuous suture is shown, which upon finishing, the suture is sealed with adhesive compounds (Bio-glue type).

FIG. 7b: Atrial prosthesis outer wing is sutured as in (1).

FIG. 7c: Sealing of the outer wing at the suture level with adhesive agglutinating biological compounds.

FIG. 7d: Upon placement of the atrial prosthesis at the left atrial wall, a small cut (stab incision) at the center of the isolated atrial wall area is done, blood loss from the left atrium is controlled with the surgeon slight finger pressure for allowing introduction of a thin catheter which has a balloon mounted at the end (balloon catheter) thereof, which is immediately filled with saline solution to avoid blood loss by means of a gentle tension. Further, the atrial wall is excised into four quadrants which facilitates removing the triangular shape of each separate quadrant flush to the base of the implanted left atrium prosthesis.

FIG. 7e: Then, without removing the catheter-balloon, the surgeon sutures the atrial prosthesis to the upper end of the special designed blood inflow pump's connector. Reference 23 designates the titanium ring which is incorporated to the base of the atrial prosthesis to maintain the atriostomy area for an undetermined period of time.

In the figures, the same reference numerals designate the same or equivalent parts.

Figure 1:
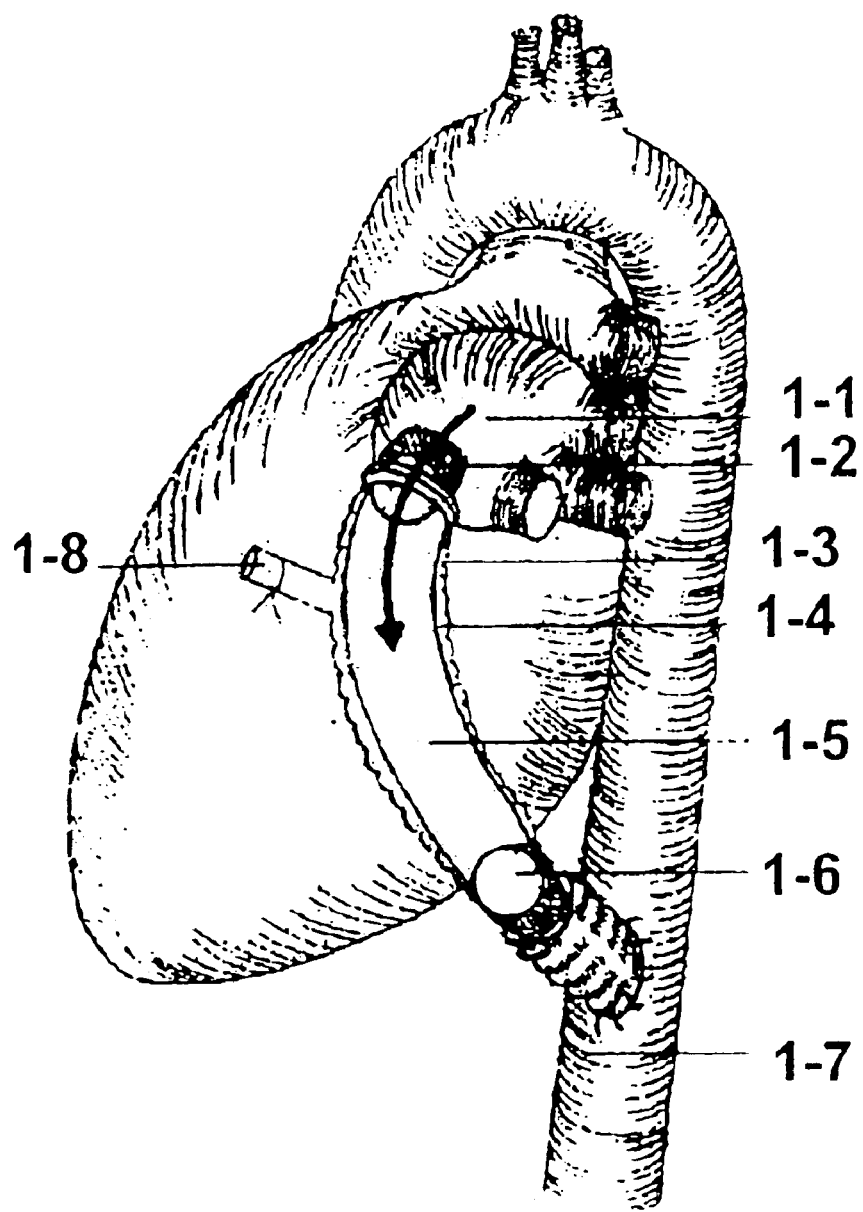
FIG. 1 shows the clinical pump of the prior art.
Figure 2:
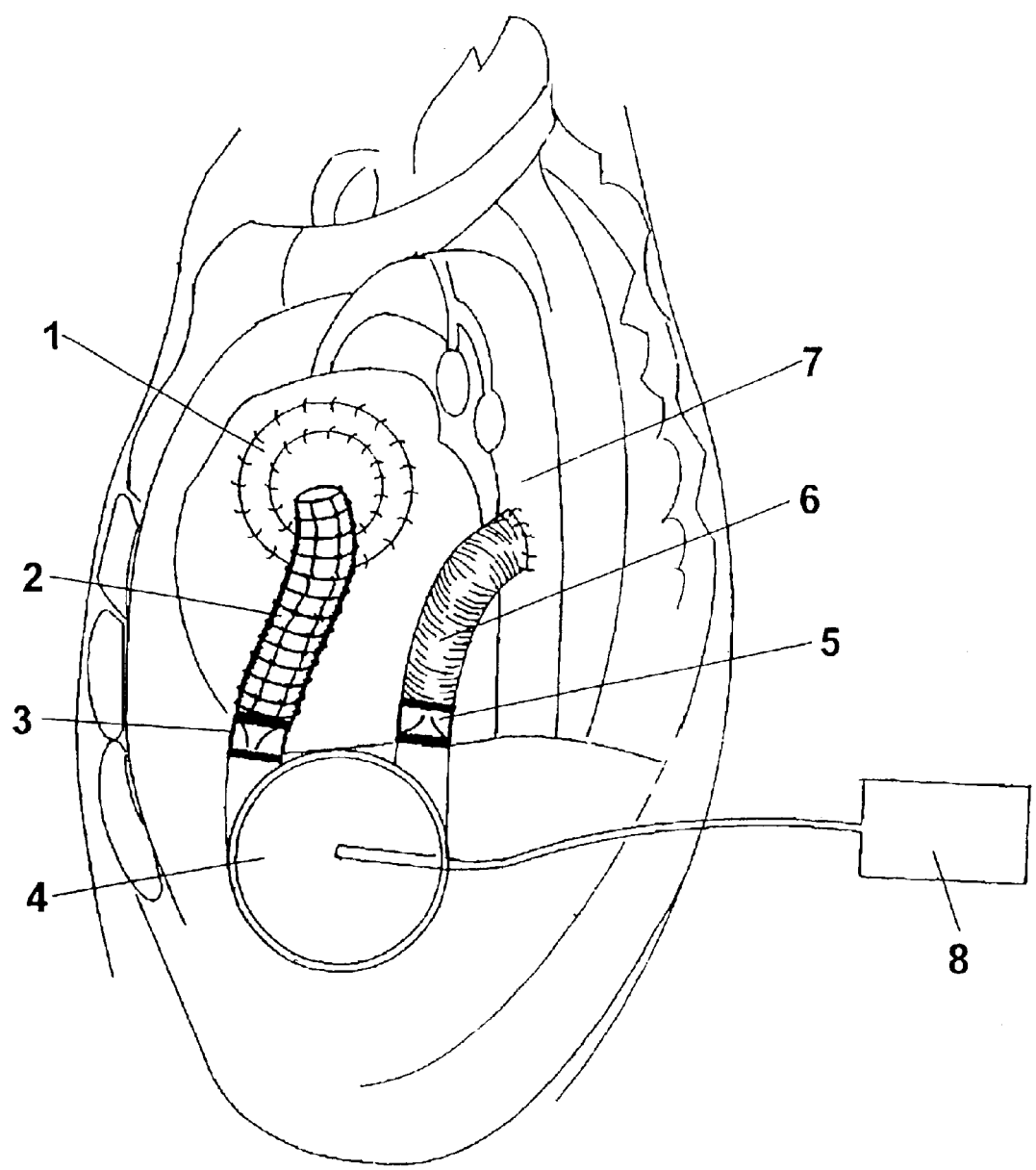
FIG. 2 is a scheme of the assembly, showing the device implanted in the body, wherein the general constitution and the arrangement of the forming elements are shown.
Figure 3A:
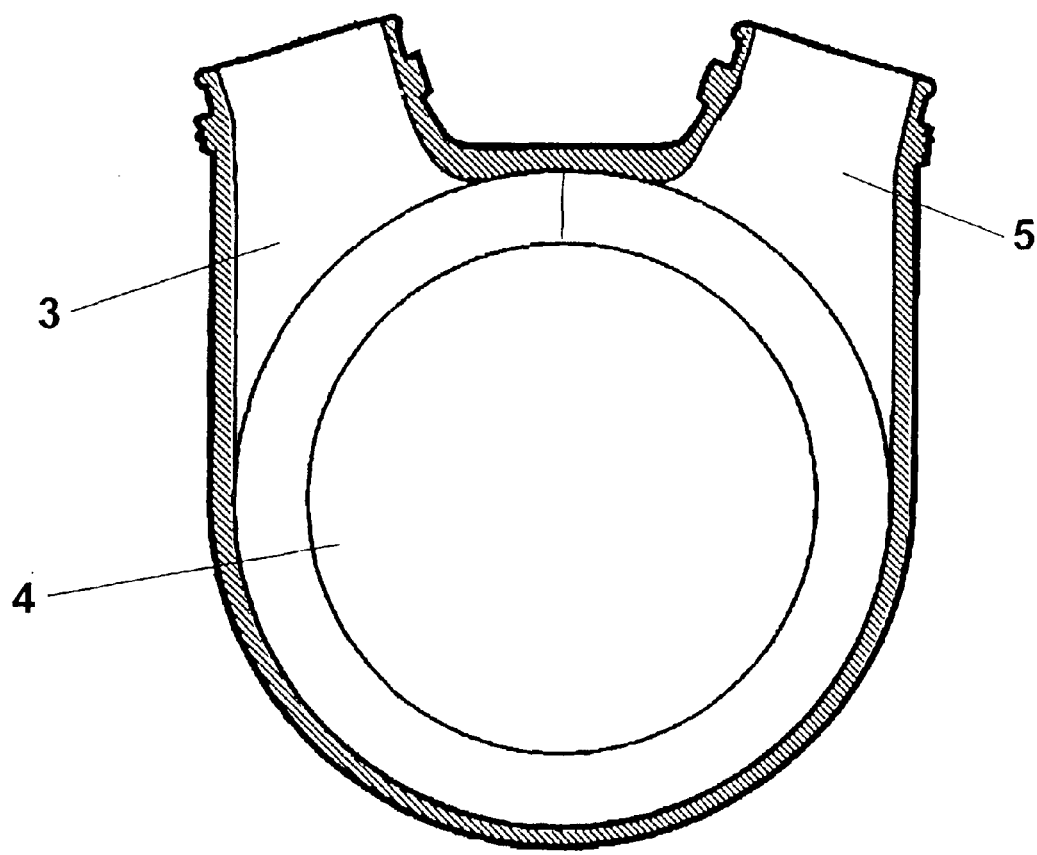
FIG. 3a shows a frontal view of the blood pump and FIG. 3b is a trasverse section through line A—A showing in a top view the inlet and outlet connectors at the pump's base. The pump body is made of titanium for medical use or, alternatively, of transparent polyurethane for medical use.
Figure 3B:
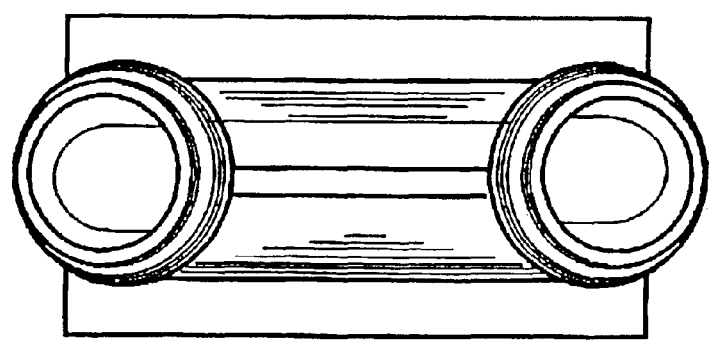
Figure 6:
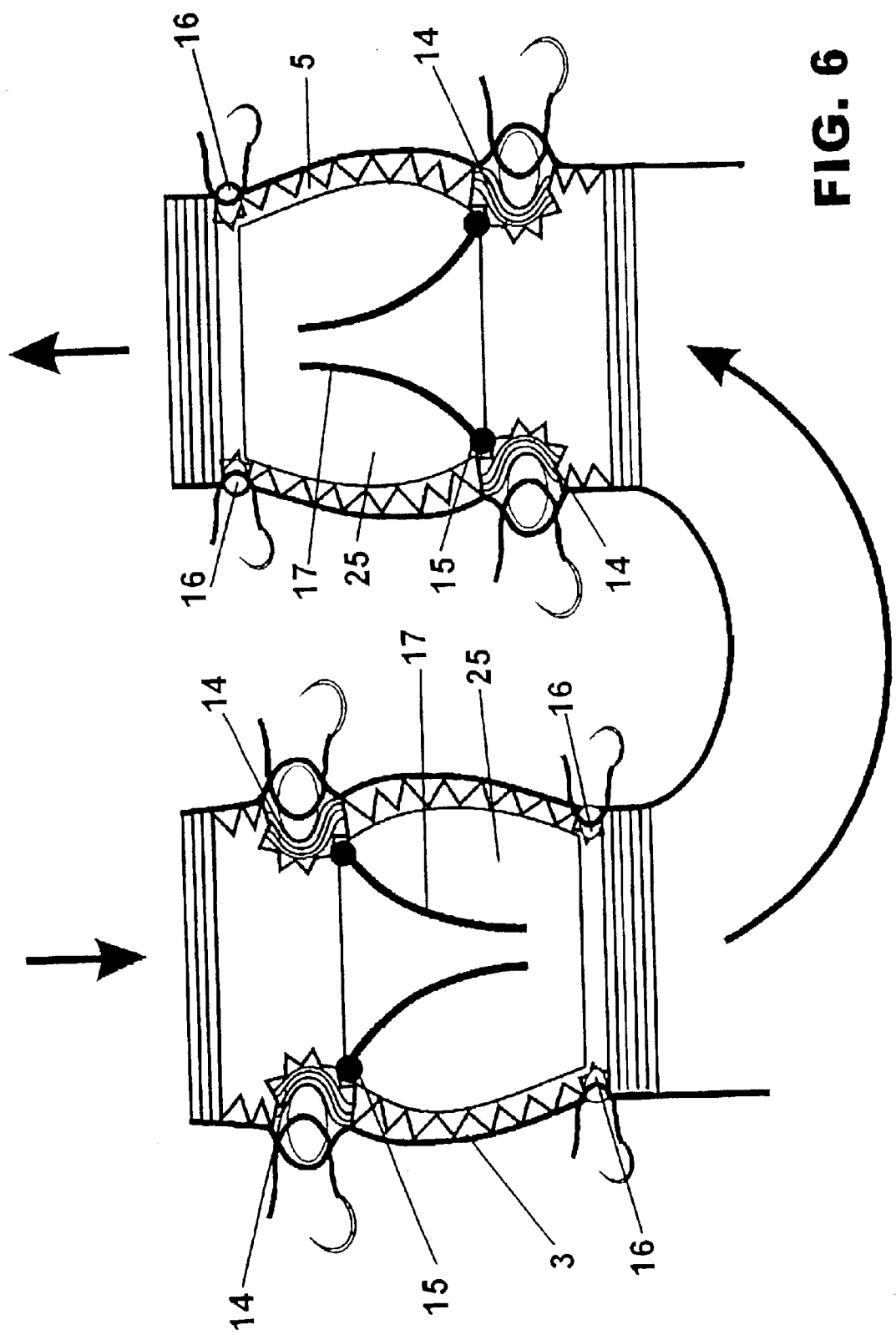
FIG. 6 is a scheme of the biological valves in which the aortic root (Valsalva sinuses) and the sino-tubular junction which joins the three commissures of the aortic valve leaflets have been preserved. The shock absorber at the seat of the valve support is particularly noted. In fact, the shock absorber at the level of the valve base (the bottom of the valve support) is crucial to avoid the valve stress which is always present when biological valves are mounted to inextensible material of the valve support. Suture rings of biological valves also play the indirect role of shock absorbers. The walls of the valve support chambers are made of medical grade titanium or of biocompatible, transparent, hard polyurethane.
Figure 7:
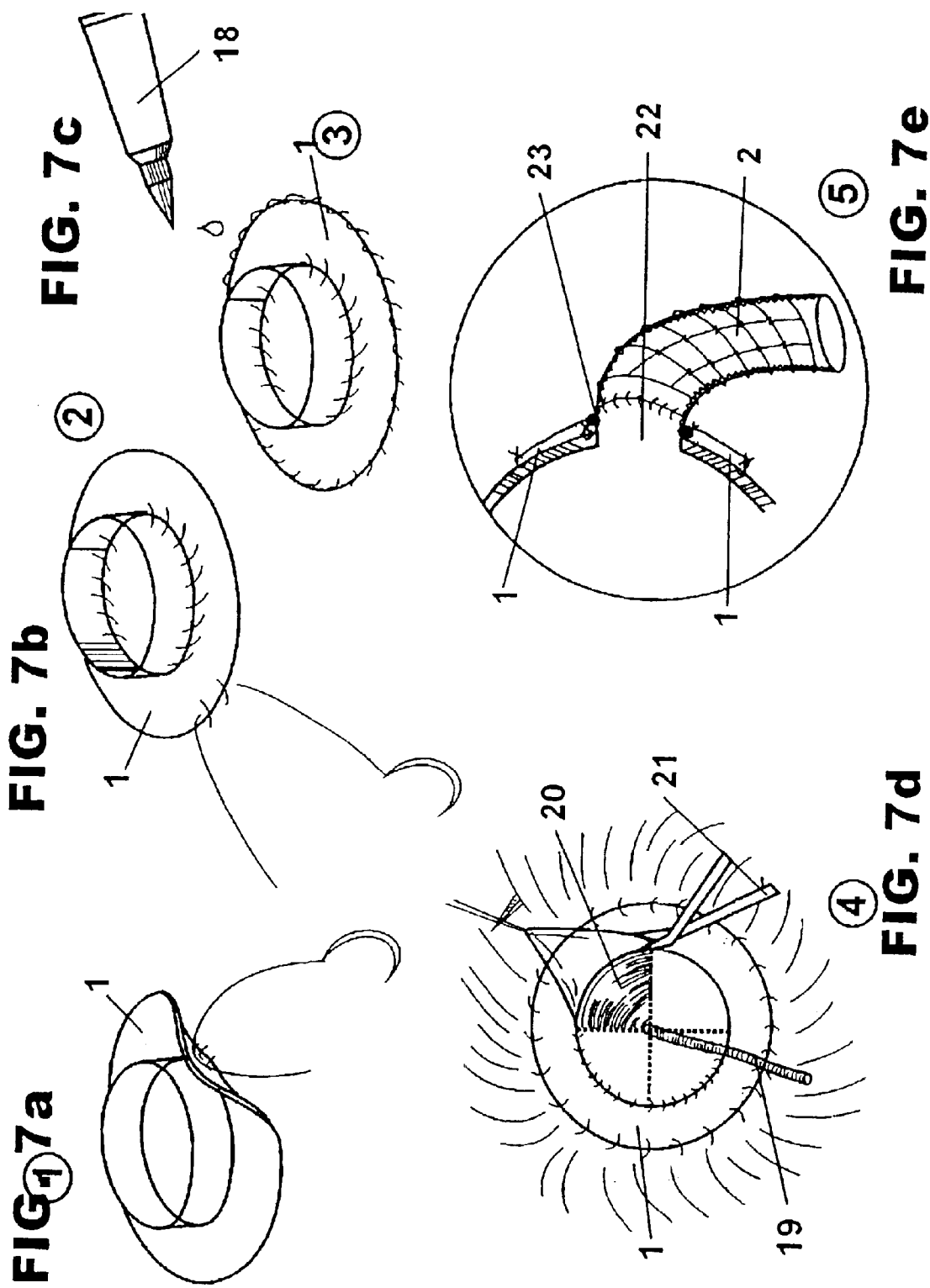
FIGS. 7a, 7b, 7c, 7d and 7e show the different steps (1 to 5) of the surgical technique for the insertion and the suturing of the atrial prosthesis with the atriostomy method and without cardiac arrest, such as when using extracorporeal circulation. In fact, during the practice of atriostomy with the method of the invention, the heart continues beating normally (beating heart). The patient is not under total extracorporeal circulation (patient off-pump). In this method, blood intake to fill the pump is done through the atriostomy, cannulae into the heart chambers are deleted, thus preventing a highly regrettable side effect, such as thromboembolic episodes, mainly brain embolism. In hemodynamically unstable patients partial extra-corporeal circulation with the heart beating should be advisable. Steps involved in the drawings.

List of the Main Reference Symbols:
(1—1)–(1-8)—References of FIG. 1 (Prior Art).
(1) Atrial prosthesis.
(2) Inlet tubular conduit.
(3) Receptacle (housing) (4) inlet.
(4) Receptacle (housing).
(5) Receptacle (housing) (4) outlet.
(6) Tubular arterial graft outlet.
(7) Descending Thoracic Aorta.
(8) Pulsating pneumatic auxiliary external device.
(9) Gas diffuser
(10) Pneumatic connection.
(11) Pneumatic variable chamber.

(12) Circulation variable chamber (blood chamber).
(13) Compression plates (pusher plates).
(14) Shock absorbers.
(15) Valve (17) inlet ring
(16) Suture at the outlet valve (adjacent to the sino-tubular junction.
(17) Inlet and outlet valves.
(18) Biological adhesive (biological adhesive).
(19) Probe (balloon catheter).
(20) Wall of the left atrium.
(21) Divider (cutter), (scissor)
(22) Atriostomy area.
(23) Atrial prosthesis titanium ring (1) rigid annular support of the atrial area.
(24) Receptacle (housing) fixing mesh
(25) Preserved aortic root and sino-tubular junction of porcine aortic valve.
(26) Holes of mesh (9).

MAIN OBJECT

The corporal implantation device for assisting blood and heart ventricular circulation; which is implanted as a blood pumping means for assisting circulation between a heart chamber and a vessel (7) of the blood circulating system, is characterized by comprising:
a) a receptacle (housing) (4) provided with an inlet (3) and an outlet (5) having means for connecting to the heart cavity and to the vessel (7);
b) inlet and outlet valves (17) in said inlet (3) and outlet (5), respectively;
c) said valves (17) determining unidirectional blood flow circulation through at least one circulation variable chamber (12);
d) there being, adjacent said circulation variable chamber (12), at least one pneumatic variable chamber (11), as a means for compressing said circulation variable chamber (12);
e) between said circulation (12) and pneumatic (11) variable chambers there being at least one compressing plate (13) cooperating with the action of said pneumatic variable chamber (11);
f) each pneumatic variable chamber (11) being connected to an external auxiliary pulsating pneumatic unit (8).

DETAILED DESCRIPTION OF THE INVENTION

The instant invention relates to a corporal implantation device for assisting blood and heart ventricular circulation.

More particularly, it relates to a blood pumping device which may be implanted into the body to assist circulation between a heart chamber [for example, an atrium or a ventricle] and a vessel (7) of the native blood circulating system [e.g., the aortic artery].

The device of the present invention comprises a receptacle (housing) (4) provided with a main body, an inlet (3) and an outlet (5).

Walls of said receptacle (4) may be rigid or semi-rigid. Also, these walls may be transparent to facilitate viewing inside during insertion.

The material of the receptacle (4) should be biocompatible, for example it may be medical grade titanium or polyurethane. In the case of titanium, it may be of the type obtained by rolling and stamping. In the case of polyurethane, it may be of hard polyurethane obtained by injection molding at high pressure of the material, or of vacuum molded laminated material.

Figure 8:
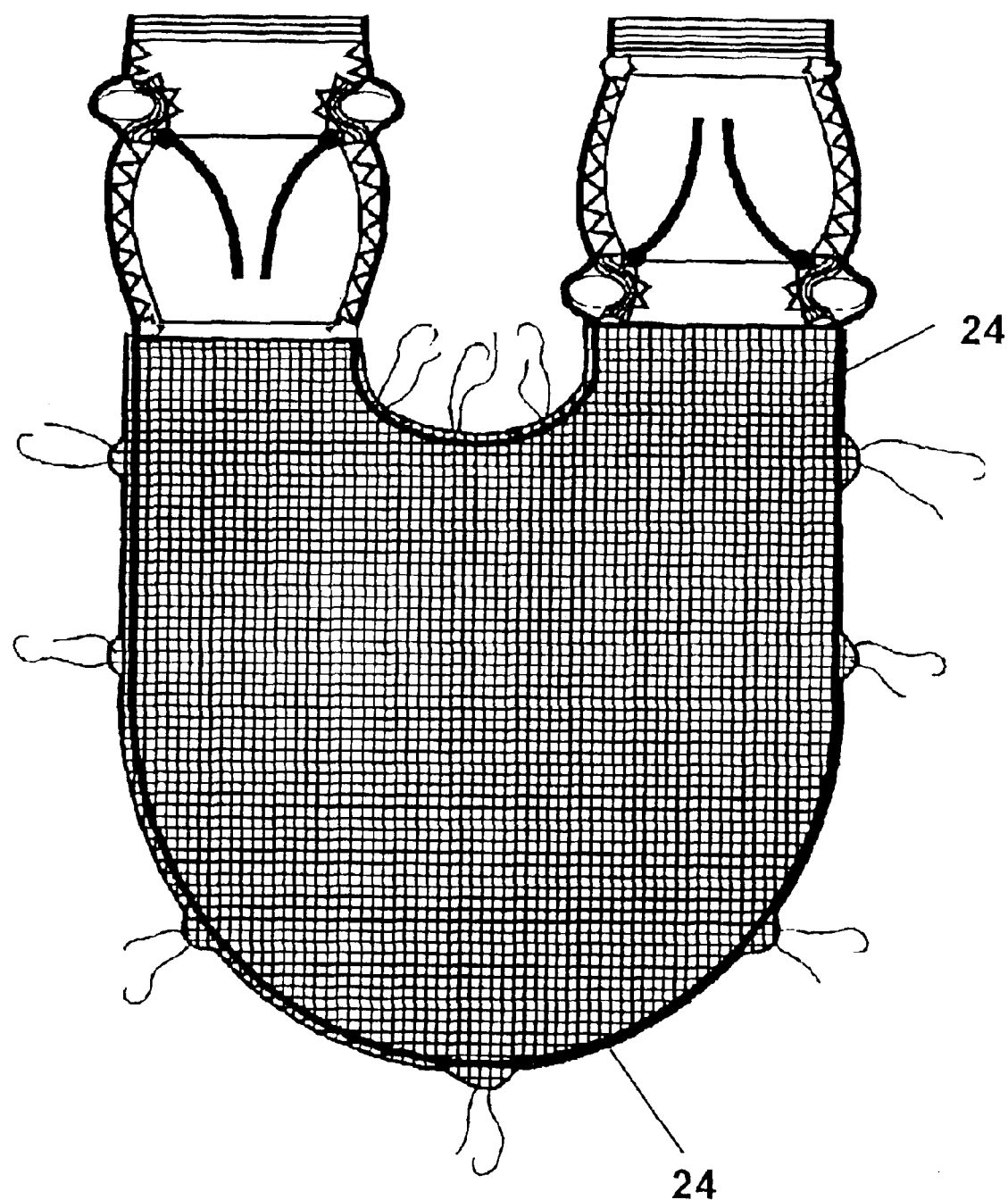
FIG. 8 is a further embodiment.

Further, an embodiment has been foreseen (FIG. 8) in which the receptacle (4) outer walls are coated with a compact cloth or by a mesh (24) of fine woven cloth made of synthetic, biocompatible material. This mesh (24) serves to fix the device to organs such as diaphragm, costal planes or muscles in an intraperitoneal position in the body. In an alternative embodiment, only the superfitial face of the receptacle (4) is partially covered by the mesh.

Inlet (3) of receptacle (4) has the means for attaching to the heart chamber, while the outlet (5) has the means for connecting to the vessel (7).

At the inlet (3) and outlet (5) of receptacle (4) there are respective inlet and outlet valves (17) determining unidirectional circulation of the blood flow therethrough.

Such valves (17) may be mechanical or biological valves. Materials constituting the valve chambers may be, among others, titanium or high hardness polyurethane.

It has been foreseen that, in a preferred embodiment of the invention, valves (17) be provided with a support including a shock absorber (14) mainly for the closing movement. This shock absorber (14) is bent upon each valve closure. It comprises either a Dacron woven element molded forming an arch or a resilient material incorporated around the valve support seat.

Inside the main body of the receptacle (4) there is a unidirectional variable blood circulation chamber (12) and two pneumatic variable chambers (11).

The circulation variable chamber (blood chamber) (12) comprises a bag having flexible walls which may be deformed by contraction and expansion. It is provided with corresponding openings by means of which it communicates to the inlet (3) and to the outlet (5) of the receptacle (4), wherein corresponding valves (17) are located.

Adjacent the circulation variable chamber (12) there is a pair of side pneumatic variable chambers (11) acting as means for compressing the circulation chamber (12) to eject blood towards the outlet (5) of receptacle (4).

Said pneumatic variable chambers (11) may comprise flexible wall bags located between the receptacle (4) walls and the circulation variable chamber (12), or they may comprise simple cavities limited by said receptacle (housing) walls and said circulation variable chamber (12).

Flexible bags forming the variable chambers (11) (12) may be made of flexible medical grade polyurethane, obtained by repeated immersion (dipping procedure), by injection molding under high pressure or by vacuum molding.

At the contact region between pneumatic variable chambers (11) and the circulation variable chamber (12) there is a set of compressing plates (pusher plates) (13) cooperating with the action of the pneumatic chambers (11) over the circulation variable chamber (12).

These compressing plates (13) may be made of polyurethane. In one of the embodiments, they may have relatively flexible strips, as a means for transmitting linear contraction of the skeletal muscle (Argentine Patent N° 254,8989 and U.S. Pat. No. 5,456,715)

Within each pneumatic variable chamber (11) a pneumatic diffuser (9) may be included, consisting of a plate which, having a plurality of holes (26), is interposed between the connection with the pulsating pneumatic auxiliary unit (8) and the circulation variable chamber (12).

In an alternative embodiment, the plurality of holes (26) of the pneumatic flow diffuser (9) are concentrated at the bottom thereof, proximally to the receptacle apex and distally with respect to the inlet region (3) and outlet region (5) thereof.

On the other hand, pneumatic variable chambers (11) are connected (10) to a pulsating pneumatic auxiliary unit (driver) (8).

The pulsating pneumatic auxiliary unit (8) is mainly comprised by a portable box containing its forming elements; a pneumatic compressing engine supplying reverse pressures; a set of electrovalves which, monitored by an electronic circuit with microcontrollers, actuate the blood filling and ejection stages of receptacle (4); rechargeable batteries; and an emergency redundant unit.

In a further alternative embodiment, the pulsating pneumatic auxiliary unit (8) comprises two identical units, similar and redundant, interconnected by means of an automatic switching circuit acting at intervals determined by a timer circuit. It also includes an alarm signaling failure of each redundant unit.

Surgical Process

The left ventricular assist system (LVAS) of the invention may be installed with the blood intake for filling the pump directly from the left ventricle chamber inserting a 20 mm ID cannula through its apex, as shown in FIG. 1 of Argentine patent No. 254,898 and U.S. Pat. No. 5,456,715. In this case, the process is applied to extremely urgent cases in which it is required the application of extra corporeal circulation to maintain the patient alive or also during conventional heart surgery in which the patient, after surgical process, is under cardiogenic shock (stunning heart with viable myocardial tissue). In these cases, the approach to have access to the patient's thoracic cavity is by means of a median sternotomy and the graft-connector of the pump outlet must be sutured to the ascending aorta or to the aortic arch.

Further, in the instant invention and provided the patient is hemodynamically stable which allows a programmed assistance, the heart is reached through a left thoracotomy The suture to the wall of the left atrium with the special atrial prosthesis has been already disclosed. In this case, filling of blood during diastolic period of the pump is carried out by means of the atriostomy, without introducing cannulae into the heart chambers and with the patient's heart beating. This is the selected technique, mainly with the process is intended for recovering the ill cardiac muscle (LVAS-bridge to myocardial recovery).

Upon practicing the invention, it is obvious that modifications may be introduced concerning construction and shape details, without departing from the basic principles of the invention as indicated in the annexed claims.

What is claimed is:

1. Corporal implantation device for assisting blood and heart vertricular circulation which is to be inserted as a blood pumping means for assisting circulation between a heart chamber and a vessel of the natural blood circulating system, comprising:
   a) a receptacle provided with an inlet and an outlet having means for connecting to a heart chamber and to a vessel;
   b) inlet and outlet valves in said inlet and outlet, respectively;
   c) said valves determining unidirectional circulation through at least one circulation variable chamber;
   d) there being, adjacent said circulation variable chamber, at least one pneumatic variable chamber, as a means for compressing said circulation variable chamber;
   e) between said circulation and pneumatic variable chambers there being at least one compressing plate cooperating with the action of said pneumatic variable chamber;
   f) the at least one pneumatic variable chamber being connected to an external auxiliary pulsating pneumatic unit, wherein the pneumatic variable chamber comprises a cavity which is connected to the pulsating pneumatic auxiliary unit and is limited by walls of the receptacle and flexible walls of the circulation variable chamber, and wherein the pneumatic variable chamber includes a pneumatic flow diffuser, wherein the pneumatic flow diffuser comprises a plate having a plurality of holes wherein the plate is interposed between the connection with the pulsating pneumatic auxiliary unit and the circulation variable chamber.

2. A device as claimed in claim 1, wherein the plurality of holes of the pneumatic flow diffuser is concentrated at a bottom of the diffuser, proximally to a receptacle apex and distally to an inlet and outlet region.

3. A device as claimed in claim 1, wherein the circulation variable chamber comprises a bag having flexible walls deformable by contraction and expansion, provided with corresponding openings by means of which it is communicated with the inlet and outlet of the receptacle, wherein the corresponding valves are housed.

4. A device as claimed in claim 1, wherein the receptacle walls are rigid.

5. A device as claimed in claim 1, wherein the receptacle walls are semi-rigid.

6. A device as claimed in claim 1, wherein the receptacle walls are transparent.

7. A device as claimed in claim 1, wherein the receptacle walls are made of a biocompatible material.

8. A device as claimed in claim 7, wherein the biocompatible material is titanium.

9. A device as claimed in claim 7, wherein the biocompatible material is medical grade polyurethane.

10. A device as claimed in claim 9, wherein the biocompatible material is titanium obtained by a rolling and stamping process.

11. A device as claimed in claim 9, wherein the biocompatible material is hard polyurethane obtained by injection molding under pressure.

12. A device as claimed in claim 9, wherein the biocompatible material is laminated polyurethane subject to vacuum molding.

13. A device as claimed in claims 1, wherein the circulation and pneumatic variable chambers are comprised by corresponding bags made of flexible medical grade polyurethane.

14. A device as claimed in claim 13, wherein flexible bags constituting circulation and pneumatic variable chambers are made of flexible medical grade polyurethane obtained by the repeated immersion process.

15. A device as claimed in claim 13, wherein flexible bags constituting circulation and pneumatic variable chambers are made of flexible medical grade polyurethane obtained by injection molding of the material under high pressure.

16. A device as claimed in claim 13, wherein flexible bags constituting circulation and pneumatic variable chambers are made of flexible medical grade polyurethane obtained by vacuum molding.

17. A device as claimed in claim 1, wherein the at least one comprising plate is made of polyurethane.

18. A device as claimed in claim 1, wherein the diffuser is made of polyurethane.

19. A device as claimed in claim 1, wherein the valves are mechanical valves.

20. A device as claimed in claim 1, wherein the valves are biological valves.

21. A device as claimed in claim 1, wherein the device further comprises valve chambers made of titanium.

22. A device as claimed in claim 1, wherein the device further comprises valve chambers made of high hardness polyurethane.

23. A device as claimed in claim 1, wherein each valve has a support with shock absorber mainly for its closing movement; said shock absorber, capable of bending at each valve closure, comprises either a Dacron cloth member molded as an arch or a resilient material incorporated around a valve support seat.

24. A device as claimed in claim 1, wherein the pulsating pneumatic external auxiliary unit is synchronized with the patient's electrocardiogram and comprises:
   a) a portable box containing forming elements;
   b) a pneumatic compressing engine supplying reverse pressures;
   c) electrovalves which, monitored by an electronic circuit with microcontrollers, actuate the blood filling and ejection stages;
   d) rechargeable batteries; and
   e) an emergency redundant unit.

25. A device as claimed in claim 24, wherein the pulsating pneumatic external auxiliary unit is a double identical unit and comprises two identical redundant units interconnected by an automatic switching circuit at intervals determined by a timer circuit.

26. A device as claimed in claim 25, wherein the double pulsating pneumatic external auxiliary unit comprise a failure alarm for each unit component.

27. A device as claimed in claim 1, wherein the at least one comprising plate has relatively flexible strips for transmitting linear contraction of the skeletal muscle.

28. A device as claimed in claim 1, wherein at least one of the receptacle walls has an outer surface coating as corporal fixing means.

29. A device as claimed in claim 28, wherein the coating is a mesh.

30. A device as claimed in claim 28, wherein the coating is a compact cloth.

31. A device as claimed in claim 29, wherein the mesh is a fine woven cloth made of biocompatible synthetic material.

32. A device as claimed in claim 1, wherein the means for connecting to a heart chamber and a vessel comprise an atrial prosthesis configured to be sutured to the wall of the left atrium, a tubular inlet conduit engaging said atrial prosthesis with the receptacle inlet and a tubular outlet conduit configured to engage the receptacle outlet with the application vessel.

33. A device as claimed in claim 32, wherein the atrial prosthesis comprises an annular base, a tubular portion and an annular support, fixed around an intersection of said annular base and said tubular portion, wherein the annular support maintains structural shape of the prosthesis and the left atrium chamber.

34. A device as claimed in claim 32, wherein the tubular inlet conduit is interiorly coated by medical fabric.

35. A device as claimed in claim 34, wherein the tubular conduit comprises a structure formed of a flexible metal spiral which is resistant to collapse and occlusion.

* * * * *